US012239634B2

(12) United States Patent
Rosen et al.

(10) Patent No.: US 12,239,634 B2
(45) Date of Patent: *Mar. 4, 2025

(54) METHODS OF TREATING PRURITUS

(71) Applicant: Clexio Biosciences Ltd., Jerusalem (IL)

(72) Inventors: Yael Rosen, Jerusalem (IL); David Dangoor, Jerusalem (IL); Richard Fisher, Jerusalem (IL)

(73) Assignee: CLEXIO BIOSCIENCES LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/483,615

(22) Filed: Oct. 10, 2023

(65) Prior Publication Data

US 2024/0033252 A1    Feb. 1, 2024

Related U.S. Application Data

(63) Continuation of application No. 17/516,871, filed on Nov. 2, 2021, now Pat. No. 11,903,928, which is a continuation of application No. 16/864,400, filed on May 1, 2020, now Pat. No. 11,185,532.

(60) Provisional application No. 62/960,027, filed on Jan. 12, 2020, provisional application No. 62/862,481, filed on Jun. 17, 2019, provisional application No. 62/841,373, filed on May 1, 2019.

(51) Int. Cl.
| A61K 31/4164 | (2006.01) |
| *A61K 9/00* | (2006.01) |
| *A61K 31/4174* | (2006.01) |
| *A61K 45/06* | (2006.01) |
| *A61P 17/04* | (2006.01) |

(52) U.S. Cl.
CPC ........ *A61K 31/4174* (2013.01); *A61K 9/0014* (2013.01); *A61K 45/06* (2013.01); *A61P 17/04* (2018.01)

(58) Field of Classification Search
CPC ............................ A61K 31/4164; A61P 17/04
USPC ........................................................ 514/396
See application file for complete search history.

(56) References Cited

U.S. PATENT DOCUMENTS

| 6,147,102 A | 11/2000 | Borgman |
| 6,225,343 B1 | 5/2001 | Behl et al. |
| 6,534,048 B1 | 3/2003 | Borgman |
| 6,627,210 B2 | 9/2003 | Olejnik et al. |
| 7,141,597 B2 | 11/2006 | Chow et al. |
| 7,345,065 B2 | 3/2008 | Gil et al. |
| 7,439,241 B2 | 10/2008 | Dejovin et al. |
| 7,812,049 B2 | 10/2010 | Shanler et al. |
| 7,838,563 B2 | 11/2010 | Dejovin et al. |
| RE41,998 E | 12/2010 | Campbell |
| 8,026,266 B2 | 9/2011 | Campbell |
| 8,053,427 B1 | 11/2011 | Buge et al. |
| 8,114,898 B2 | 2/2012 | Shanler et al. |
| 8,231,885 B2 | 7/2012 | Dejovin et al. |
| 8,394,800 B2 | 3/2013 | Dejovin |
| 8,513,247 B2 | 8/2013 | Graeber et al. |
| 8,911,713 B2 | 12/2014 | Bouvier et al. |
| 9,186,358 B2 | 11/2015 | Jomard et al. |
| 11,185,532 B2 | 11/2021 | Rosen et al. |
| 11,903,928 B2 * | 2/2024 | Rosen .................... A61P 17/04 |
| 2004/0266776 A1 | 12/2004 | Gil et al. |
| 2005/0020600 A1 | 1/2005 | Scherer |
| 2005/0058696 A1 | 3/2005 | Donello et al. |
| 2005/0059744 A1 | 3/2005 | Donello et al. |
| 2007/0048335 A1 | 3/2007 | Gil et al. |
| 2009/0061020 A1 | 3/2009 | Theobald et al. |
| 2010/0029610 A1 | 2/2010 | Singh et al. |
| 2011/0118267 A1 | 5/2011 | DeJovin |
| 2012/0076738 A1 | 3/2012 | Graeber et al. |
| 2012/0101104 A1 | 4/2012 | Buge et al. |
| 2012/0201863 A1 | 8/2012 | John et al. |
| 2013/0023572 A1 | 1/2013 | Dibas et al. |
| 2013/0029989 A1 | 1/2013 | Coderre et al. |
| 2013/0079379 A1 | 3/2013 | Shanler et al. |
| 2013/0184283 A1 | 7/2013 | Dejovin |
| 2013/0190317 A1 | 7/2013 | Chappuis et al. |
| 2015/0098982 A1 | 4/2015 | Pongpeerapat et al. |
| 2015/0313895 A1 | 11/2015 | Graeber et al. |
| 2015/0313896 A1 | 11/2015 | Bouvier et al. |
| 2016/0331715 A1 | 11/2016 | Buge et al. |
| 2017/0348291 A1 | 12/2017 | Vainio et al. |
| 2019/0343805 A1 | 11/2019 | Tsipori et al. |

FOREIGN PATENT DOCUMENTS

| CN | 104788427 A | 7/2015 |
| EP | 2501373 A1 | 9/2012 |
| GB | 2256135 A | 12/1992 |
| JP | 2005-075735 A | 3/2005 |
| WO | 92/21338 A1 | 12/1992 |
| WO | 2004/052347 A1 | 6/2004 |

(Continued)

OTHER PUBLICATIONS

Andersen et al., "Itch, Topography of itch: evidence of distinct coding for pruriception in the trigeminal nerve", Mar. 2017, vol. 2, No. e02, pp. 1-10.

Anonymous: "Alpha-adrenergic agonist: Difference between revisions—Wikipedia", Apr. 27, 2019, XP055701386, retrieved from the internet: URL:https://en.wikipedia.org/w/index.php?title=Alpha-adnergic_agonist&diff=894393512&oldid=893237280 (retrieved on Jun. 5, 2020).

Benkali et al., "Comparative pharmacokinetics and bioavailability of brimonidine following ocular and dermal administration of brimonidine tartrate ophthalmic solution and gel in patients with moderate-to-severe facial erythema associated with rosacea", British Journal of Dermatology, 2014, vol. 171, pp. 162-169.

(Continued)

*Primary Examiner* — Raymond J Henley, III
(74) *Attorney, Agent, or Firm* — BakerHostetler

(57) ABSTRACT

The present disclosure related to methods of treating pruritus in a subject by topically administering detomidine, or a pharmaceutically acceptable salt thereof, to the subject.

20 Claims, 3 Drawing Sheets

(56) References Cited

FOREIGN PATENT DOCUMENTS

| | | | |
|---|---|---|---|
| WO | 2006/048501 A1 | 5/2006 |
| WO | 2008/079727 A2 | 7/2008 |
| WO | 2009/158477 A1 | 12/2009 |
| WO | 2011/060295 A1 | 5/2011 |
| WO | 2011/075267 A1 | 6/2011 |
| WO | 2011/085162 A2 | 7/2011 |
| WO | 2011/117377 A2 | 9/2011 |
| WO | 2011/117378 A2 | 9/2011 |
| WO | 2012/052478 A2 | 4/2012 |
| WO | 2012/052479 A2 | 4/2012 |
| WO | 2012/075319 A2 | 6/2012 |
| WO | 2012/083397 A1 | 6/2012 |
| WO | 2013/014448 A1 | 1/2013 |
| WO | 2015/191917 A1 | 12/2015 |
| WO | 2018/129313 A1 | 7/2018 |
| WO | 2020/012415 A2 | 1/2020 |

OTHER PUBLICATIONS

Blume, Fungal Acne vs Bacterial Acne. Retrieved from the internet on Jun. 1, 2023, https://www.blume.com/blogs/blume-university/fungal-acne-vs-bacterial-acne. (Year: 2023).

Campbell et al., "Mechanisms of Neuropathic Pain", Neuron, Oct. 5, 2006, vol. 52, No. 1, pp. 77-92.

Carstens et al., "The Challenge of Basic Itch Research", Acta Derm. Venereol., 2020, vol. 100, pp. 1-7.

Charifa et al., "Lichen Simplex Chronicus", [Updated May 2, 2023], In: StatPearls [Internet], Treasure Island (FL): StatPearls, Publishing Year: 2023, pp. 1-7.

Davis et al., "Pain, Topical application of clonidine relieves hyperalgesia in patients with sympathetically maintained pain", Pain, 1991, vol. 47, pp. 309-317.

Dormosedan Gel Label, detomidine hydrochloride 7.6 mg/ml oromucosal gel, Product Brochure, 2009, pp. 1-8.

Ellis, "Notalgia paresthetica: the unreachable itch", Dermatol. Pract. Concept, Jan. 2013, vol. 3, No. 1, pp. 3-6.

FDA Product Label Cleocin T, Topical Clarithromycin, May 30, 2003, pp. 1-5.

FDA Product Label E Glades, Generic Name: Erythromycin Topical Gel, USP, 2%, Mar. 18, 2002, pp. 1-79.

FDA Product Label Metrolotion, Topical Metronidazole Lotion, Aug. 2003, pp. 1-2.

FDA Product Label Noritate, Topical Metronidazole Cream, Apr. 2003, pp. 1-4 pages.

Giovannoni et al., "a2-Agonists as Analgesic Agents", Medicinal Research Reviews, 2009, vol. 29, No. 2, pp. 339-368.

Gotoh et al., "Clonidine inhibits itch-related response through stimulation of a2-adrenoceptors in the spinal cord in mice", European Journal of Pharmacology, 2011, vol. 650, pp. 215-219.

Han et al., "A Subpopulation of Nociceptors Specifically Linked to Itch", Nature Neuroscience, 2013, vol. 16, pp. 174-182.

International Application No. PCT/IB2020/054140, International Search Report and Written Opinion, Jul. 21, 2020, pp. 1-23.

Ishikawa et al., "Investigation of the Correlation Between Postherpetic Itch and Neuropathic Pain Over Time", Hindawi Pain Research Management, Article ID 9305126, 2018, pp. 1-6.

Jin et al., "Ocular Hypotensive Effects of Medetomidine and Its Analogs", Journal of Ocular Pharmacology and Therapeutics, Jan. 1991, vol. 7, No. 4, pp. 285-296.

Johnson et al., "Method for Comparison of the Hemodynamic Effects of Equi-Antinociceptive Oral Doses of Drugs in Anesthetized Rats", J. Pharmacol. Toxicol., 1999, vol. 42, pp. 127-133.

Khan et al., "Alpha-2 and imidazoline receptor agonists Their pharmacology and therapeutic role", Anaesthesia, 1999, vol. 54, pp. 146-165.

Khasar et al., "Peripheral Nociceptive effects of a2-Adrenergic receptor agonists in the rat", Neuroscience, 1995, vol. 66, No. 2, pp. 427-432.

Kuraishi, Pharmacology of Itch; Noradrenergic Modulation of Itch Transmission in the Spinal Cord, 2015, pp. 207-217.

Ladizinski et al., "Lichen amyloidosis", CMAJ., Apr. 15, 2014, 186(7), 532.

Li et al., "Effects of Topical Application of Clonidine Cream on Pain Behaviors and Spinal Fos Protein Expression in Rat Models of Neuropathic Pain, Postoperative Pain, and Inflammatory Pain", Anesthesiology, 2007, vol. 107, pp. 486-494.

Matasushita et al., "Adrenergic receptors inhibit TRPV1 activity in the dorsal root ganglion neurons of rats", PLoS One, 2018, vol. 13, No. 1, e0191032, pp. 1-15.

Matsuda et al., "Gabapentin and pregabalin for the treatment of chronic pruritus", JAAD., Sep. 2016, vol. 75, Issue 3, pp. 619-625. e6.

Schaper-Gerhardt et al., "The role of the histamine H4 receptor in atopic dermatitis and psoriasis", Br. J. Pharmacology, Feb. 2020, vol. 177, No. 3, pp. 490-502.

Schmelz, "Itch and Pain Differences and Commonalities", Handbook Exp. Pharmacology, 2015, vol. 227, pp. 285-301.

Schwartz et al., "Affinity of detomidine, medetomidine and xylazine for alpha-2 adrenergic receptor subtypes", J. Vet. Pharmacol. Therap., 1998, vol. 21, pp. 107-111.

Seifert et al., "Paradoxical Stimulatory Effects of the "Standard" Histamine H4-Receptor Antagonist JNJ7777120: the H4 Receptor Joins the Club of 7 Transmembrane Domain Receptors Exhibiting Functional Selectivity", Mol Pharmacol., Apr. 2011, vol. 79, No. 4, pp. 631-638.

Song et al., "Pruritus: Progress toward Pathogenesis and Treatment", BioMed Research International, vol. 2018, Article ID 9625936, pp. 1-12.

Steinhoff et al., "Clinical presentation, management, and pathophysiology of neuropathic itch", Lancet Neurol., Aug. 2018, vol. 17, No. 8, pp. 709-720.

Taylor et al., "Pruritus, Cleveland Clinic, Definition and etiology", Retrieved from the internet on Jul. 28, 2023, https://www.clevelandclinicmeded.com/medicalpubs/diseasemanagement/dermatology/pruritus-itch/#:~:text=Definition%20and%20etiology,-Pruritus%20or%20itch&text=It%20is%20a%20characteristic%20feature,sign%20of%20some%20 (Year: 2010).

Thibaut et al., "Distinct Behavioral Response of Primary Motor cortex Stimulation in Itch and Pain After Burn Injury", Neuroscience Letters, Oct. 2018, pp. 1-24.

Thurmond et al., "The histamine H4 receptor: from orphan to the clinic", Frontiers Pharmacology, Mar. 2015, vol. 6 Art 65, pp. 1-11.

Virtanen et al., "Antinociceptive activity and mechanism of action of detorqidine", J. Vet. Pharmacol. Therap., 1986, vol. 9, pp. 286-292.

Virtanen et al., "Evaluation of the a-1 and a2-Adrenoceptor effects of Detomidine, a novel veterinary sedative analgesic", European Journal of Pharmacology, 1985, vol. 108, pp. 163-169.

Wikipedia, "Alpha-Adrenergic Agonist: Difference Between Revisions", Downloaded on May 6, 2020, pp. 1-4.

Wrzosek et al, "Topical clonidine for neuropathic pain (Review)", The Cochrane Collaboration, 2015, vol. 36, pp. 1-34.

Yosipovitch et al., "Itch: From mechanism to (novel) therapeutic approaches", J. Allergy Clin. Immunol., Nov. 2018, vol. 142, No. 5, pp. 1375-1390.

Zeigler et al., "Transdermal clonidine versus placebo in painful diabetic neuropathy", Pain, 1992, pp. 403-408.

"Highlights of Prescribing Information These highlights do not include all the information needed to use MIRVASO® safely and effectively. See full prescribing information for MIRVASO", Nov. 2017, pp. 2.

Allersmeier et al., "Effects of dermal dexamethasone application on ACTH and both basal and ACTH-stimulated cortisol concentration in normal horses", vol. 32, Issue 4, Aug. 2009, 379-387.

Baron et al., "Role of adrenergic transmitters and receptors in nerve and tissue injury related pain", Mechanisms and Mediators of Neuropathic Pain, 2002, pp. 153-174.

Bronaugh et al., "Differential rates of percutaneous absorption through the eczematous and normal skin of a monkey", J Invest Dermatol, 1986, vol. 87, No. 4, pp. 451-453.

(56) References Cited

OTHER PUBLICATIONS

Dai Tijun et al., "Progress in Anesthesiopharmacology", Second Military Medical University Press, Jul. 31, 2012, p. 126.
DaSilva-Arnold et al., "Phenotyping acute and chronic atopic dermatitis-like lesions in Stat6VT mice identifies a role for IL-33 in disease pathogenesis", Arch Dermatol Res. 2018, vol. 310, No. 3, pp. 197-207.
Fujimoto, Mycotoxins: Classification, Occurrence and Determination, Yeasts and Molds | Mycotoxins: Classification, Occurrence and Determination, 2011, pp. 792-800.
Genois et al., "Case Report of Atopic Dermatitis with Refractory Pruritus Markedly Improved with the Novel Use of Clonidine and Trimeprazine", Pediatric Dermatology, 2014, vol. 31 No. 1, pp. 76-79.
Griffiths et al., "Rook's Textbook of Dermatology", Ninth edition, 2016, pp. 9.
Haddadi et al., "Possible Involvement of Nitric Oxide in the Antipruritic Effect of Metformin on Chloroquine-Induced Scratching in Mice", Dermatology, Aug. 22, vol. 236, No. 2, 2019, pp. 1-9.
Holmes et al., Dermatological Adverse Events Associated with Topical Brimonidine Gel 0.33% in Subjects with Erythema of Rosacea, A Retrospective Review of Clinical Studies, Aug. 2015, vol. 8, No. 8, pp. 29-35.
Kaczmarska et al., "Pathomechanism of Pruritus in Psoriasis and Atopic Dermatitis: Novel Approaches, Similarities and Differences", Int. J. Mol. Sci., Sep. 29, 2023, vol. 24, 14734, pp. 1-21.
Ketoconazole—ketoconazole shampoo, suspension, Padagis Israel Pharmaceuticals Ltd, Ketoconazole Shampoo, 2%, RX only, 2022.
Kim et al., "Major medical causes by breed and life stage for dogs presented at veterinary clinics in the Republic of Korea: a survey of electronic medical records", 2018, 1-23.
Lowenthal et al., "Clinical Pharmacokinetics of Clonidine", Clinical Pharmacokinetics, 1988, vol. 14, pp. 287-310.
Ma et al., "The Neuropeptide Y Y2 Receptor Is Coexpressed with Nppb in Primary Afferent Neurons and Y2 Activation Reduces Histaminergic and IL-31-Induced Itch", J Pharmacol Exp Ther., Jan. 2020, vol. 372, pp. 73-82.
Marino et al., "Development and validation of an automated system for detection and assessment of scratching in the rodent", Journal of Neuroscience Methods, Aug. 1, 2012, vol. 211, pp. 1-10.
Matthews et al., "Serum metabolomics using ultra performance liquid chromatography coupled to mass spectrometry in lactating dairy cows following a single dose of sporidesmin", Metabolomics, 2018, vol. 14, No. 61, pp. 1-14.
Moore et al., "Long-Term Safety and Efficacy of Once-Daily Topical Brimonidine Tartrate Gel 0.5% for the Treatment of Moderate to Severe Facial Erythema of Rosacea: Results of a 1-Year Open-Label Study", J Drugs Dermatol., Jan. 2014, vol. 13, No. 1, pp. 56-61.
Patterson's Allergic Diseases, Seventh Edition, 1997, pp. 502-504.
Pereira et al., "PIEZO1 channels in cutaneous free nerve endings: novel insights into itch-scratch-mechanisms", Signal Transduction and Targeted Therapy, Jan. 2, 2023, vol. 8, No. 4, pp. 1-2.
Phua et al., "Identifying chromosomal selection-sweep regions in facial eczema selection-line animals using an ovine 50K-SNP array", vol. 45, Issue 2, Apr. 2014, pp. 240-247.
Reid et al., "Parenteral exposure to detomidine and butorphanol", J Toxicol Clin Toxicol., 1994, vol. 32, No. 4, pp. 465-469.
Sanders et al., "Modulation of Itch by Localized Skin Warming and Cooling", Acta Derm Venereol 2018; 98: 855-861.
Sekiyama et al., "ED50 of Y2 agonist transdermal administration and systemic administration: Comparative study in a mouse itch model, Journal of the Japanese Society of Pain Clinics, 2006, vol. 13, No. 3, p. 320", Journal of the Japan Society of pain clinicians.
Sekiyama, "Antipruritic Effect of Y2-Adrenergic Receptor Agonists", Journal of the Japanese Society of Pain Clinics, 2007, vol. 14, No. 2, pp. 160-161.
Selenium Sulfide—selenium sulfide shampoo Bi-Coastal Pharma International LLC, Selenium Sulfide, 2.25% Shampoo, Rx Only, 2022.
Szepietowski et al., Itching in Patients Suffering from Psoriasis, Acta Dermat Croat, 2002, vol. 10, No. 4, pp. 221-226.
Zhang et al., "3'-O-Methylorobol Inhibits the Voltage-Gated Sodium Channel Nav1.7 with Anti-Itch Efficacy in A Histamine-Dependent Itch Mouse Model", Int J Mol Sci., Dec. 1, 2019, vol. 20, No. 23, 6058, pp. 1-15.

* cited by examiner

METHODS OF TREATING PRURITUS

CROSS REFERENCE TO RELATED APPLICATIONS

This application is a continuation of U.S. Ser. No. 17/516,871, filed Nov. 2, 2021, which is a continuation of U.S. application Ser. No. 16/864,400, filed May 1, 2020 (now U.S. Pat. No. 11,185,532), which claims the benefit of U.S. Provisional Application Nos. 62/841,373, filed May 1, 2019, 62/862,481, filed Jun. 17, 2019, and 62/960,027, filed Jan. 12, 2020, the entire contents of each of which are incorporated herein by reference.

TECHNICAL FIELD

The present disclosure related to methods of treating pruritus in a subject by topically administering detomidine, or a pharmaceutically acceptable salt thereof, to the subject.

BACKGROUND

Pruritus is an unpleasant sensation that provokes the desire to scratch. The condition is extremely common with estimates that at any given time between 8 and 16% of adults are suffering from it, resulting in significant reductions in quality of life for sufferers. To date, despite numerous attempts at clinical studies, no drug has been approved to treat the condition.

Detomidine is a synthetic alpha-2 adrenoreceptor agonist with sedative and analgesic properties. It is presently sold by prescription under the trade name DORMOSEDAN® (Zoetis Services LLC, Parsippany, NJ) as a sedative and anesthetic premedication in connection with a variety of minor surgical and diagnostic procedures on horses and other large animals. It is commonly combined with butorphanol in order to increase the degree of analgesia and depth of sedation, and may also be used with ketamine for intravenous anesthesia of short duration. The route of administration of DORMOSEDAN® injection is typically intramuscular or intravenous, but the drug is also available as a gel (DORMOSEDAN GEL®) that may be administered by the sublingual route. More recently, detomidine has been shown to be effective as a topical analgesic agent.

SUMMARY OF THE INVENTION

The present invention relates to the topical treatment of pruritus by detomidine.

DETAILED DESCRIPTION

Figure 1:
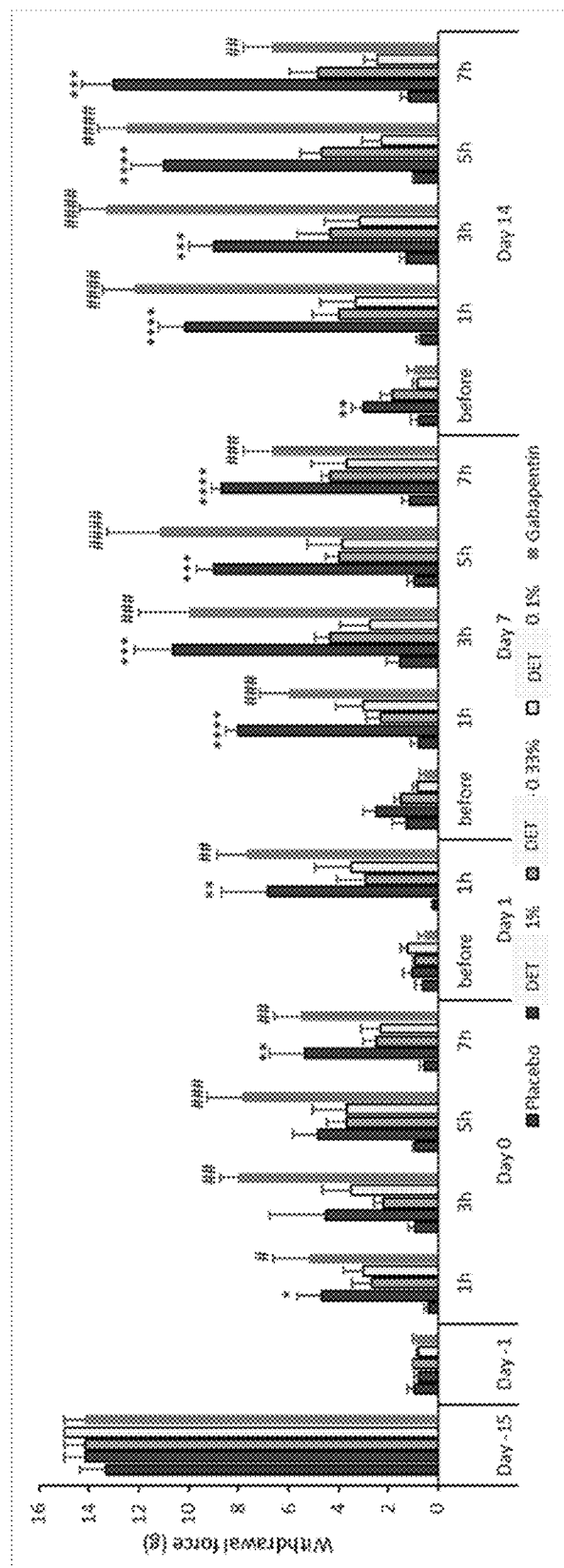
FIG. 1: A graphical representation of mechanical sensitivity over time.

The present inventions may be understood more readily by reference to the following detailed description taken in connection with any accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a particle" is a reference to one or more of such particles and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably refers to a value of 7.2% to 8.8%, inclusive. Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included." The phrase "at least about x" is intended to embrace both "about x" and "at least x". It is also understood that where a parameter range is provided, all integers within that range, and tenths thereof, are also provided by the invention. For example, "2-5 hours" includes 2 hours, 2.1 hours, 2.2 hours, 2.3 hours etc . . . up to 5 hours.

"Subject," as used herein, includes humans and animals. The terms "human," "patient," and "subject" are used interchangeably herein.

The present invention relates to methods of treating pruritus in a subject comprising topically administering to the subject's skin, detomidine or a pharmaceutical composition comprising detomidine. According to the invention, the amount of detomidine topically administered to the subject is sufficient to treat pruritus. Pruritus can be demonstrated to have been treated by reductions in VAS, NRS, Quality of Life and/or pruritus scores or by other methods known in the art.

The detomidine may be topically administered as the free base form or as a salt. Unless specified otherwise, reference to "detomidine" in the present disclosure can refer to detomidine in a free base form, or to a salt of detomidine. Those of ordinary skill in the art can readily identify exemplary pharmaceutically acceptable salt forms of detomidine. Suitable pharmaceutically acceptable salts of detomidine include detomidine bitartrate, detomidine bitartrate hydrate, detomidine hydrochloride, detomidine p-toluenesulfonate, detomidine phosphate, detomidine thiosemicarbazone, detomidine sulfate, detomidine trifluoroacetate, detomidine hemipentahydrate, detomidine bitartrate hemipentahydrate, detomidine pentafluoropropionate, detomidine p-nitrophenylhydrazone, detomidine o-methyloxime, detomidine semicarbazone, detomidine hydrobromide, detomidine mucate, detomidine oleate, detomidine phosphate dibasic, detomidine phosphate monobasic, detomidine inorganic salt, detomidine organic salt, detomidine acetate trihydrate, detomidine bis(heptafluorobutyrate), detomidine bis(methylcarbamate), detomidine bis(pentafluoropropionate), detomidine bis(pyridine carboxylate), detomidine bis(trifluoroacetate), detomidine chlorhydrate, and detomidine sulfate pentahydrate. In certain embodiments of the presently disclosed dosage forms, the detomidine is present as the hydrochloride salt. In certain embodiments, the detomidine is anhydrous detomidine hydrochloride. In other embodiments, the detomidine is detomidine hydrochloride monohydrate.

In some embodiments, the pruritus is acute. Acute pruritus is the defined as the manifestation of the condition for up to six consecutive weeks. In other embodiments, the pruritus is chronic. Chronic pruritus is defined as the manifestation of the condition for more than six consecutive weeks.

In certain embodiments, the origin of the pruritus is unknown. In other embodiments, the pruritus comprises the symptom of a dermatological, neurological, psychogenic or systemic condition, or is of mixed origin.

Examples of pruritic dermatological conditions include atopic dermatitis, contact dermatitis, allergic dermatitis, seborrheic dermatitis, statis dermatitis, pityriasis rubra pilaris, pityriasis rosea, acne, dermatitis herpetiformis, pemphigus vulgaris, bullous pemphigoid, lichen planus, prurigo nodularis, lichen simplex chronicus, lichen amyloidosis, urticaria, mastocytosis, polymorphous light eruption, actinic prurigo, chronic prurigo, actinic dermatitis, polymorphic eruption of pregnancy, eosinophilic folliculitis, dermatomyositis, prurigo pigmentosa, lichen sclerosus, palmoplantar pustulosis, pompholyx, idiopathic xerosis, scarring, burns, burn scars, keloid scars, hypertrophic scars, reactive drug eruptions and pruritus of an infestive or infective origin.

Examples of pruritic infestive conditions include scabies, pediculosis and arthropod bites.

Examples of pruritic infective conditions include fungal, parasitic, viral and bacterial conditions.

Examples of pruritic neurological conditions include notalgia paresthetica, brachioradial pruritus, postherpetic neuralgia, stroke, small fiber neuropathy, trigeminal trophic syndrome, Creutzfeldt-Jakob disease, chemotherapy-induced neuropathy, HIV-related neuropathy and multiple sclerosis.

Examples of pruritic psychogenic conditions include depression, anxiety, psychogenic excoriation, anorexia nervosa and delusional parasitosis.

Examples of pruritic systemic conditions include chronic renal failure, uremic pruritus, liver disease, primary biliary cholangitis, primary biliary cirrhosis, cholestatic jaundice, hepatitis C, cholestasis of pregnancy, polycythemia vera, iron deficiency anemia, Hodgkin lymphoma, non-Hodgkin lymphoma, multiple myeloma, hematologic or lymphoproliferative disorders, primary cutaneous lymphoma, mycosis fungoides, cutaneous T cell lymphoma, malignancy, plasma cell dyscrasias, gastric carcinoid tumors, hyperthyroidism, hypothyroidism, hyperparathyroidism, haemochromatosis, celiac disease, systemic lupus erythematosus, systemic sclerosis, diabetes, carcinoid syndrome, dermatomyositis, scleroderma, Sjögren's syndrome, linear immunoglobulin A (IgA) disease, graft-versus-host disease, Darier disease, Hailey-Hailey disease, porphyria and amyloidosis.

Pruritus is understood to occur when pruritogens activate receptors on small itch-selective unmyelinated C-fibers. Two subtypes of itch-sensitive neurons are found in the dermal tissues, histaminergic and non-histaminergic neurons, each with different tracts and different patterns of brain activation.

Histaminergic neurons are primarily involved in acute pruritus. Histamine is released by mast cells and other immune cells and keratinocytes. H1 and H4 receptors on histaminergic nerves bind histamine and activate TRPV1 through the phospholipase system. The excited histaminergic neurons also release neuropeptides such as calcitonin gene-related protein and substance P, which can cause inflammatory effects such as local vasodilation, plasma extravasation, and mast cell degranulation.

Non-histaminergic neurons can be excited by endogenous/exogenous pruritogens other than histamine and express various receptors involved in pruritus. These receptors activate either TRPV1 or TRPA1 through the phospholipase or kinase system.

As shown in WO2018129313, which is incorporated herein in its entirety, detomidine has been demonstrated to be effective as a topical agent for the treatment of pain. Without wanting to be bound to any particular theory, it is believed that when administered topically, detomidine can inhibit peripheral pruritus signal transduction in a similar manner to its inhibition of peripheral pain signal transduction. Furthermore, in addition to its well established use as an alpha-2 adrenoreceptor agonist, surprisingly, it has now been found that detomidine possesses a variety of additional receptor binding properties which are believed to contribute to its ability to topically treat pruritus.

In certain embodiments, the detomidine is administered topically in pharmaceutical compositions comprising about 0.01 to about 5 wt % of detomidine. For example, the pharmaceutical compositions comprise about 0.01, 0.02, 0.03, 0.033, 0.04, 0.05, 0.06, 0.066, 0.07, 0.09, 0.1, 0.2, 0.3, 0.33, 0.4, 0.5, 0.6, 0.66, 0.7, 0.8, 0.9, 1, 1.33, 1.5, 1.66, 2, 2.33, 2.5, 2.66, 3, 3.33, 3.5, 3.66, 4, 4.33, 4.5, 4.66 or 5 wt % of detomidine. In certain embodiments, the pharmaceutical compositions comprise 0.033, 0.1, 0.33 or 1 wt % of detomidine. In a preferred embodiment, the pharmaceutical composition comprises 0.1 wt % of detomidine. In another preferred embodiment, the pharmaceutical composition comprises 0.33 wt % of detomidine. In another preferred embodiment, the pharmaceutical composition comprises 1 wt % of detomidine.

In certain embodiments, the topically administered detomidine is the only, or sole, active agent being administered to treat pruritus. In other embodiments, the topically administered detomidine is administered in combination with at least one additional active agent. In certain embodiments, the additional active agent is also administered topically, either in a combined, or as separate, pharmaceutical compositions. In other embodiments, the additional active agent is administered orally or parenterally. Examples of parenteral administration include intravenous, intramuscular, subcutaneous, rectal, sublingual, buccal, inhaled and intrathecal administrations.

Examples of additional active agents include corticosteroids, doxepine, tacrolimus, pimecrolimus, pramoxine, lidocaine, prilocaine, ketamine, amitriptyline, capsaicin, menthol, camphor, strontium, tofacitinib, crisaborole, N-palmitoylethanolamine, antihistamines, SNRIs, SSRIs, naltrexone, butophanol, nalfurafine, gabapentin, pregabalin, aprepitant, thalidomide, lenalidomide, ursodeoxycholic acid, rifampin, cholestyramine, phenobarbital, Botulinum toxin A, naloxone, ASN008, SNA-125, TS-022, KPL-716 and orvepitant.

Examples of corticosteroids include alclometasone, amcinonide, beclometasone, betamethasone, budesonide, ciclesonide, clobetasol, clobetasone, clocortolone, cortisone, desonide, desoximetasone, dexamethasone, diflorasone, fluocinolone, fluocortolone, fluprednidene, flurandrenolide, fluticasone, halcinonide, halobetasol, halometasone, hydrocortisone, mometasone, methylprednisolone, prednicarbate, prednisolone, prednisone, tixocortol, triamcinolone and mometasone.

Examples of anti-histamines include acrivastine, azelastine, bilastine, bromodiphenhydramine, brompheniramine, buclizine, carbinoxamine, cetirizine, chlorodiphenhydramine, chlorpheniramine, clemastine, cyclizine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocabastine, levocetirizine, loratadine, meclizine, mirtazapine, olopatadine, orphenadrine, phenindamine, pheniramine, phenyltoloxamine, promethazine, pyrilamine, rupatadine, tripelennamine and triprolidine.

Examples of SNRIs include venlafaxine, duloxetine, milnacipran, mirtazapine and levomilnacipran.

Examples of SSRIs include fluoxetine, fluvoxamine, paroxetine, sertraline, citalopram and escitalopram.

In certain embodiments, the detomidine is topically administered once daily to treat pruritus. In other embodiments, the detomidine is topically administered twice daily to treat pruritus. In other embodiments, the detomidine is topically administered three times daily to treat pruritus.

Detomidine is administered topically to treat pruritus in the form of a pharmaceutical composition. Examples of pharmaceutical compositions for the topical administration of detomidine to treat pruritus include gels, creams, ointments, emulsions, emu-gels, foams, suspensions and spray-patches. In a preferred embodiment, the detomidine is topically administered in the form of a gel.

In one embodiment, the present invention relates to a method of treating pruritus comprising the topical administration of a 0.033 wt % gel of detomidine. In another embodiment, the present invention relates to a method of treating pruritus comprising the topical administration of a 0.1 wt % gel of detomidine. In another embodiment, the present invention relates to a method of treating pruritus comprising the topical administration of a 0.33 wt % gel of detomidine. In another embodiment, the present invention relates to a method of treating pruritus comprising the topical administration of a 1 wt % gel of detomidine. In one embodiment, the administration is once daily. In another embodiment, the administration is twice daily.

Topical administration of the pharmaceutical compositions to a subject can result in a blood plasma concentration in the subject that is less than that required to achieve a systemic therapeutic effect of the detomidine. Preferably, the topical administration can continue for weeks, months, or longer while maintaining a sub-therapeutic systemic blood plasma concentration and with minimal or no medically relevant effect outside of that bodily region, or simply minimal or no medically relevant systemic effect.

In certain embodiments, the pharmaceutical compositions of the present invention provide prolonged, substantially non-systemic treatment for pruritus. The period of time over which the pharmaceutical compositions can provide treatment for pruritus is up to 24 hours when topically applied once a day. In certain embodiments, the pharmaceutical compositions are preferably applied twice per day, and in such instances the treatment of pruritus that is provided by a first of the two topical administrations has a duration that lasts until the second topical administration, and the second daily topical administration has a duration that lasts until the following day's first topical administration. As used herein, "substantially non-systemic" refers to a treatment effect that is localized to the bodily region (for example, body part) to which the pharmaceutical compositions is topically applied, with a minimal or no medically relevant effect outside of that bodily region, or simply no minimal or no medically relevant systemic effect.

Examples of gels, creams, ointments, emulsions, emu-gels, foams, suspensions and spray-patches of detomidine are described in WO2018129313 and WO2020012415, each of which are incorporated herein by reference in their entireties.

The pharmaceutical compositions of detomidine for topical administration can also include a carrier that is suitable for topical administration to a subject's skin. The carrier may include, for example, a solubilizer, a buffer, or both. The carrier can also be a mixture of a hydrophilic phase member and a hydrophobic phase member. As described below, the formulation may also include one or more additional components in order to produce the topical form, such as thickening or gelling agents, preservatives, antioxidants, permeation enhancers, emulsifying agents, emollients, or humectants.

Examples of solubilizers include alcohols, such as sugar alcohols, diols, polyols, or polyether alcohols, fatty acids, organic solvents, waxes, oils, poloxamers, cyclodextrins, or any combination thereof. For example, the solubilizer may be glycerol, polyethylene glycol (such as PEG 3350), propylene glycol, poloxamer 124, poloxamer 407, Labrasol® (caprylocaproyl polyoxyl-8 glycerides), Kleptose® HPB, Captisol® sulfobutylether β-cyclodextrin, or any combination thereof. In some embodiments, the solubilizer is glycerol, propylene glycol, polyethylene glycol, or any combination thereof. For example, the water-miscible solubilizer may include both glycerol and propylene glycol.

Examples of hydrophilic phase members include water, glycerol, polypropylene glycol, polyethylene glycol, ethanol, benzyl alcohol, 1,3-propanediol, 1,2-pentanediol, propylene carbonate, 2-(2-ethoxyethoxy)ethanol, dimethyl isosorbide, tetraglycol, pyrrolidone, dimethylacetamide, caprylocaproyl polyoxyl-8 glycerides, hexylene glycol, butylene glycol, or any combination thereof. The hydrophilic phase member may also comprise an aqueous buffer solution. For example, the hydrophilic phase member may comprise 0.01 to 1.0M citrate, phosphate, Tris, carbonate, succinate, tartrate, borate, imidazole, maleate, or phthalate buffer at pH 4.5-9.0.

Examples of hydrophobic phase members include aromatic hydrocarbons, alkane, cycloalkanes, alkynes, terpenes, organic oils, mineral oils, or any combination thereof. Exemplary hydrophilic phase members include mineral oil, isopropyl isostearate, isostearyl isostearate, alkyl benzoate, butyl stearate, diisopropyl adipate, diethylhexyl adipate, caprilic/capric triglyceride, isocetyl stearate, isopropyl myristate, isopropyl palmitate, lauryl lactate, myristil myristate, ethylhexyl cocoate, ethylhexyl palmiatate, ethylhexyl pelagronate, ethylhexyl stearate, diethylhexyl succinate, propylene glycol dicaprylate/dicaprate, PPG-2 myristyl ether propionate, pentaerythrityl tetracaprylate/caprate, pentaerythrityl tetraisostearate, PEG 2 stearyl ether, steareth-21, and isotridecyl isononanoate. An exemplary genus of hydrophobic phase members is medium chain triglycerides. Further hydrophobic phase members that represent fatty acid esters are disclosed in U.S. Pub. No. 2012/0201863, the entire contents of which are incorporated herein by reference.

Examples of thickening or gelling agents can include hydroxymethyl cellulose, hydroxyethyl cellulose, hydroxypropyl cellulose, hydroxypropylmethyl cellulose, xanthan gum, carbomers (acrylates and acrylic acid and its derivatives polymers, such as Carbopol® 980 (crosslinked polyacrylate polymer)), povidones (e.g., polyvinylpyrrolidone), Poloxamers, Polyamide-3 (e.g. , OleoCraft™ HP33), and other appropriate agents.

Examples of preservatives can include benzalkonium chloride, parabens, sorbic acid and its salts, benzoic acid and its salts, cetrimonium bromide and chloride salts, phenoxyethanol, and other agents.

Examples of antioxidants can include sodium metabisulfite, ascorbic acid, tocopheryl acetate (for purely aqueous formulations), and BHT or BHA (for hydrophobic formulations).

Examples of permeation enhancers can include Transcutol® P (highly purified diethylene glycol monoethyl ether EP/NF) or dimethylisosorbide (DMI).

Examples of emulsifying agents can include Tweens, Spans, poloxamers (124, 407, 188), Brij S2 and Brij 721, Crodex M (cetearyl alcohol and potassium cetyl Phosphate), Crodafos CES (cetearyl alcohol and dicetyl phosphate and Ceteth-10 phosphate (Crodafos CES), Cithrol DPHS (PEG 30 Dipolyhydroxystearate), cyclopentasiloxane, or macrogol hydroxystearate.

Examples of emollients can include, but are not limited to, Migliol 810 or 812 (caprylic-capric triglycerides), Isoporpyl Isostearate (Crodamol IPIS), Isostearyl Isostearate (Crodamol ISIS), PPG-11 Stearyl Ether (Arlamol PS HE), Macrogol 6 Glycerol Caprylocaprate (Glycerox 767HC), or Labrasol® (caprylocaproyl polyoxyl-8 glycerides).

Examples of humectants can include, but are not limited to, glycerin, propylene glycol, 1,3-propanediol, or 1,2-pentanediol.

In certain embodiments, the topical pharmaceutical compositions comprise 0.01 to 5 wt % detomidine hydrochloride, glycerine, propylene glycol, a gelling agent, and a buffer that is effective to maintain the pharmaceutical composition at pH about 4.5 to about 8.2. In some embodiments, the topical pharmaceutical compositions comprise 0.01 to 3 wt % detomidine hydrochloride, glycerine, propylene glycol, a cellulose gelling agent, and a buffer that is effective to maintain the pharmaceutical composition at pH about 4.5 to about 6. In some other embodiments, the topical pharmaceutical compositions comprise 0.05 to 3 wt % detomidine hydrochloride, glycerine, propylene glycol, a cellulose gelling agent, and a buffer that is effective to maintain the pharmaceutical composition at pH about 5 to about 6. In yet other embodiments, the topical pharmaceutical compositions comprise 0.1 to 2 wt % detomidine hydrochloride, glycerine, propylene glycol, a cellulose gelling agent, and a buffer that is effective to maintain the pharmaceutical composition at pH about 5 to about 5.5. In still other embodiments, the topical pharmaceutical compositions comprise 0.1 to 1 wt % detomidine hydrochloride, glycerine, propylene glycol, hydroxy ethyl cellulose, and a buffer that is effective to maintain the pharmaceutical composition at pH about 5 to about 5.5. In yet other embodiments, the topical pharmaceutical compositions comprise 0.1 to 1 wt % detomidine hydrochloride, glycerine, propylene glycol, hydroxy ethyl cellulose, and a buffer that is effective to maintain the pharmaceutical composition at pH about 5.2 to about 5.5. Any of these embodiments may further comprise a preservative.

In certain embodiments, the topical pharmaceutical compositions comprise at least about 0.01 weight percent of detomidine, based on the total weight of the composition. In some embodiments, detomidine is present in an amount in the range of about 0.01 to about 0.5 weight percent. In some other embodiments, detomidine is present in an amount in the range of about 0.01 to about 0.25 weight percent. In yet another embodiment, detomidine is present in an amount in the range of about 0.01 to about 0.075 weight percent. As discussed herein, all weight percentage of detomidine is calculated based on the weight of the topical pharmaceutical composition, e.g., a gel.

The pharmaceutical compositions may include a volatile solvent that at least partially evaporates from the skin surface following application. For example, in certain embodiments, the buffer component is aqueous, and the water that is contained within the aqueous buffer represents the volatile solvent. The portion of the formulation that remains following at least partial evaporation can be referred to as the "nonvolatile" or "residual" phase, and the volatile element(s) of the formulation that evaporate from the skin surface represents the "volatile" phase.

In certain embodiments, the pharmaceutical compositions may include an inert excipient that assists with increasing the concentration of the detomidine or salt thereof in the residual phase following topical application. In effect, such excipients can cause "salting out" of the detomidine or salt thereof from the other components of the residual phase, which can have the effect of increasing the activity of the detomidine or salt thereof on the surface of the subject's skin and promote permeability of the drug through the skin. Such inert excipients can include, for example, a polyol or simple sugar, such as sucrose, dextrose, trehalose, mannitol, sorbitol, or xylitol.

In certain embodiments, pharmaceutical compositions may comprise a foam. Foams according to the present disclosure may include a hydrophobic phase member that comprises, for example, a medium chain triglyceride, mineral oil, or both. The hydrophilic phase member in the foams may include, for example, one or more of propylene glycol, hexylene glycol, 1,3-propanediol, 1,2-pentanediol or water.

The pharmaceutical compositions may comprise a cream. In cream formulations, the hydrophobic phase member may comprise, for example, mineral oil, isopropyl isostearate, isostearyl isostearate, alkyl benzoate, butyl stearate, diisopropyl adipate, diethylhexyl adipate, caprilic/capric triglyceride, isocetyl stearate, isopropyl myristate, isopropyl palmitate, lauryl lactate, myristil myristate, ethylhexyl cocoate, ethylhexyl palmiatate, ethylhexyl pelagronate, ethylhexyl stearate, diethylhexyl succinate, propylene glycol dicaprylate/dicaprate, PPG-2 myristyl ether propionate, pentaerythrityl tetracaprylate/caprate, pentaerythrityl tetraisostearate, isotridecyl isononanoate, or any combination thereof. The hydrophilic phase member may be, for example, glycerol, propylene glycol, water, 1,3-propanediol, 1,2-pentanediol, hexylene glycol, butylene glycol, or any combination thereof. Cream formulations may further comprise a fatty alcohol, an ester of a fatty alcohol, or both, an emulsifier, an emollient, or any combination thereof, including each of these components.

In accordance with the presently disclosed methods, the topical administration may be performed using conventional techniques. For example, the administration may be performed by delivering an aliquot of the pharmaceutical composition to a physician's or subject's hand, which is used to smear and then rub the pharmaceutical composition onto an area of skin on the body part for which treatment is desired. In the case of a spray patch, the pharmaceutical composition may be sprayed using any suitable mechanism, such as an aerosol, mister, spray bottle, or the like. The pharmaceutical composition may be topically administered in the chosen manner on a once-daily, twice-daily or three-times daily basis. When the method comprises applying the composition on a twice-daily basis, appropriate temporal spacing between applications should be used. For example, if the subject is awake for a 16 hour period of the day, then a first application can be performed in the morning, and a second application can be performed in the evening, for example, prior to retiring to bed.

EXAMPLES

The following examples are set forth so as to provide those of ordinary skill in the art with a complete disclosure and description of how the methods, compositions, and components claimed herein are made and evaluated, and are intended to be purely exemplary of the invention and are not intended to limit the scope of what the inventors regard as their invention.

Example 1: Topical Detomidine Gels

Topical formulations containing detomidine HCl were prepared. The prepared formulations are described in Table 1.

TABLE 1

| Formulation | 0.01% | 0.033% | 0.10% | 0.33% | 1.00% |
|---|---|---|---|---|---|
| Detomidine HCl | 0.01% | 0.03% | 0.10% | 0.33% | 1.00% |
| Hydroxyethyl cellulose (Natrosol 250HH) | 1.75% | 1.75% | 1.75% | 1.75% | 1.75% |
| Glycerin | 0.30% | 0.30% | 0.30% | 0.33% | 3% |
| Propylene Glycol | 0.10% | 0.10% | 0.10% | 1% | 1% |
| Transcutol P | 0.10% | 0.10% | | | |
| Benzalkonium Chloride as 0.5% sol in water | 0.02% | 0.02% | 0.02% | 0.02% | 0.02% |
| Ad 100% | Tris buffer 0.05M pH 8.2 | Buffer Phosphate 0.05M pH 7.2 | Buffer Citrate 0.05M pH 5.5 | Buffer Citrate 0.05M pH 5.5 | Buffer Citrate 0.2M pH 5.2 |

Example 2: In Vitro Binding Assay

Comparative radioligand binding assays of detomidine and clonidine were performed (Eurofins, Taiwan) using human recombinant cell lines. The results are shown in Table 2, with ≥50% inhibition demonstrating a significant response. All results shown are at 10 µM, identified previously unknown binding affinities for detomidine for both $H_4$ and $SST_4$ receptors.

TABLE 2

| Assay | % inhibition (detomidine) | % inhibition (clonidine) |
|---|---|---|
| Adrenergic α1A | 99 | 91 |
| Adrenergic α1B | 97 | 85 |
| Adrenergic α1D | 95 | 85 |
| Adrenergic α2A | 97 | 94 |
| Adrenergic α2B | 104 | 101 |
| Adrenergic α2C | 100 | 97 |

TABLE 2-continued

| Assay | % inhibition (detomidine) | % inhibition (clonidine) |
|---|---|---|
| Histamine H4 | 68 | 2 |
| $SST_4$ | 35 | 13 |

Example 3: In Vitro Functional Assay

Cellular and nuclear receptor functional and enzyme uptake assays of detomidine and clonidine were performed (Eurofins, France). The highest concentration tested was 10 µm and possible activity above this concentration was not determined in the assay. The results are shown in Table 3 and demonstrate that in addition to its known agonist activity for alpha adrenergic receptors, detomidine also possesses agonistic properties for both $H_4$ and $SST_4$ receptors. Both $H_4$ and $SST_4$ agonism have been identified as potential pathways for the topical treatment of various types of pruritus.

TABLE 3

| | detomidine | | clonidine | |
|---|---|---|---|---|
| | | $EC_{50}$ | | $EC_{50}$ |
| Adrenergic α1A | agonist | 1.9 nM | agonist | 3 nM |
| Adrenergic α1B | — | not determined | — | not determined |
| Adrenergic α1D | — | not determined | — | not determined |
| Adrenergic α2A | agonist | 23.5 nM | agonist | 21.7 nM |
| Adrenergic α2B | agonist | 36 nM | agonist | 30 µm |
| Adrenergic α2C | agonist | 0.3 nM | agonist | 4.4 nM |
| Histamine H4 | agonist | 4.7 µm | not tested | |
| $SST_4$ | agonist | 7.3 µm | not tested | |

Example 4: In Vitro β-Arrestin Assay

In order to determine whether detomidine functions as an $H_4$ agonist or inverse agonist, histamine (a known $H_4$ agonist), A 943931 (a known $H_4$ antagonist) and detomidine were assayed using a GPCR internalization assay which provided a quantitative measurement of arrestin-mediated GPCR internalization of $HRH_4$ (Eurofins Discover X, USA). The results are shown in Table 4 and demonstrate that detomidine is an $H_4$ agonist.

TABLE 4

| Compound | Assay format | Result type | $RC_{50}/\mu M$ |
|---|---|---|---|
| Histamine | Agonist | $EC_{50}$ | 0.03 |
| A 943931 | Antagonist | $IC_{50}$ | 0.07 |
| Detomidine | Agonist | $EC_{50}$ | 9.6 |
| | Antagonist | $IC_{50}$ | >100 |
| | Inverse agonist | $EC_{50}$ | >100 |

Example 5: Peripheral Neuritis Trauma (PNT)-Induced Neuropathic Pain in Pigs The analgesic effect of detomidine was assessed in a PNT-induced neuropathic pain in pigs (MD Biosciences/Lahav Institute of Research, Israel). 30 pigs were anaesthetized and an incision of 8 -10 cm made through the skin and fascia on the left side of their lower backs, approximately 1 cm lateral and parallel to the spine line. The muscles were retracted and the sciatic nerve exposed. Following exposure, PNT was induced by loosely tying (1-2 mm apart) around the lateral half of the sciatic nerve bundle, three 3-0 silk threads, each previously immersed in complete Freund's adjuvant.

14 days after surgery and once chronic neuropathic pain had been established, treatment was initiated according to the protocol shown in Table 5.

TABLE 5

| Treatment | No. of Animals | Dose Concentration | Dosing volume (ml) | Dosing Route and Regimen |
|---|---|---|---|---|
| Placebo | 6 | N/A | 4 mL | Topical, twice daily to the outer area of the leg innervated by the injured sciatic nerve |
| Detomidine 0.1% | 6 | 0.1% | 4 mL | |
| Detomidine 0.33% | 6 | 0.33% | | |
| Detomidine 1% | 6 | 1% | | |
| Gabapentin (positive control) | 6 | 6 mg/kg | — | IV, 1 hour prior to the 1$^{st}$ Von Frey test on Days 0, 1, 7 and 14 |

At time points over the following 14 days, the animals were assessed for a variety of pain and motor parameters. Stimulus-evoked pain was assessed using Von Frey (VF) filaments and shown to demonstrate a dose-dependent analgesic effect, with detomidine alleviating pain in, comparison to placebo, a statistically significant manner by increasing VF withdrawal threshold from Day 0 of treatment. Tactile stimulation, utilizing a 12-13 cm pigeon feather, showed that detomidine demonstrated a dose-dependent decreased tactile allodynia in response to light (non-painful) stimulus as soon as Day 0. Spontaneous pain behavior and General Behavioral Score (GBS) was assessed by monitoring solitary performance and social behavior of each animals at 3 h and 6 h post-dose and showed that detomidine demonstrated a dose-dependent reduction in GBS scores from Day 0, indicative of decreased spontaneous pain in response to treatment. An open field motor test assessed motor function and any potential sign of sedation and showed that detomidine did not affect locomotor activity at any dose level throughout the study, indicating that topical administration of detomidine did not cause any sedative effect in the animals. The results of the stimulus-evoked pain study are shown in FIG. 1. These results show topical detomidine effects in significant pathologies associated with pruritus of neuropathic origin.

Figure 2:
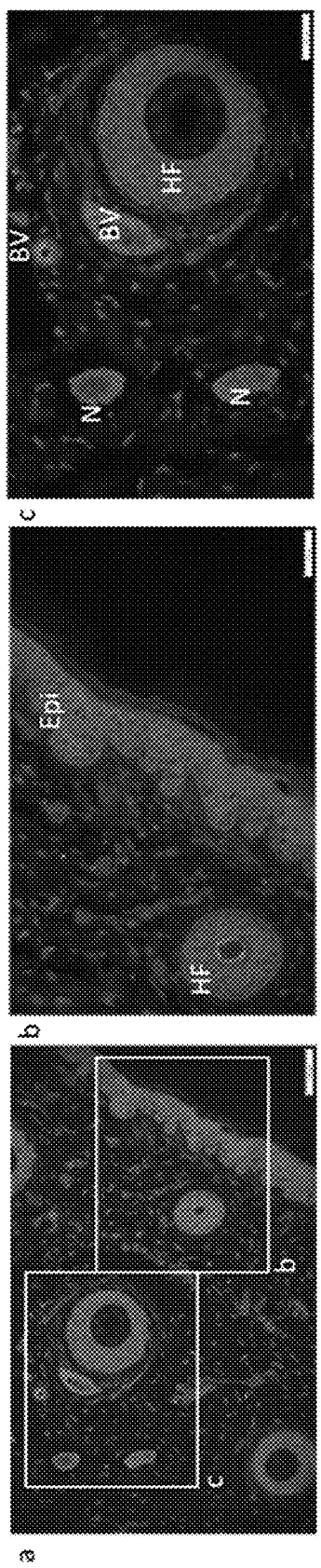
FIG. 2: Images of immunostaining of pig skin biopsies at ×200 (a) and ×400 (b, c) magnification.

Following completion of the study, skin biopsies were taken from the outer area of the leg of the placebo treated animals and immunostained using anti α2A adrenergic receptor polyclonal antibodies. Images were taken of the stained tissue using ×20 objective, total magnification ×200, scale bar 100 μm (Image a) or ×40 objective, total magnification ×400, scale bar 50 μm. (Images b and c). The results of the staining are shown in FIG. 2 and show positive staining in epidermis (full thickness) (Epi), hair follicles (HF), blood vessels (BV) and nerves (N) for α2A adrenergic receptors. These results identify the previously unknown presence of α2adrenegric receptors in the skin and local surrounding tissues, potentially allowing for substantially non-systemic amounts of detomidine to be therapeutically effective when administered topically.

Example 6: Acute Itch Model

150 μl of vehicle or 0.10%, 0.33% or 1.00% topical formulations of Example 1 were administered topically over a 2 cm$^2$ area of groups of 8 mice (4 male, 4 female) for 5 consecutive days (Days 1-5). An active control group of 8 additional mice were intraperitoneally administered a single dose of U-50,488 (CAS 67198-13-4), a selective K-opioid agonist on Day 5.

On Day 4, 2 mice (1 male, 1 female) in the 1.00% topical formulation group died, all other mice completed the treatment protocol. On Day 5, 30 minutes after the administration of either vehicle, control or detomidine, 0.4 mg of chloroquine was injected subcutaneously to the mice. The number of scratching events were recorded for each of the 5 groups at 5 minute intervals from the chloroquine administration over a 30 minute total duration.

Figure 3:
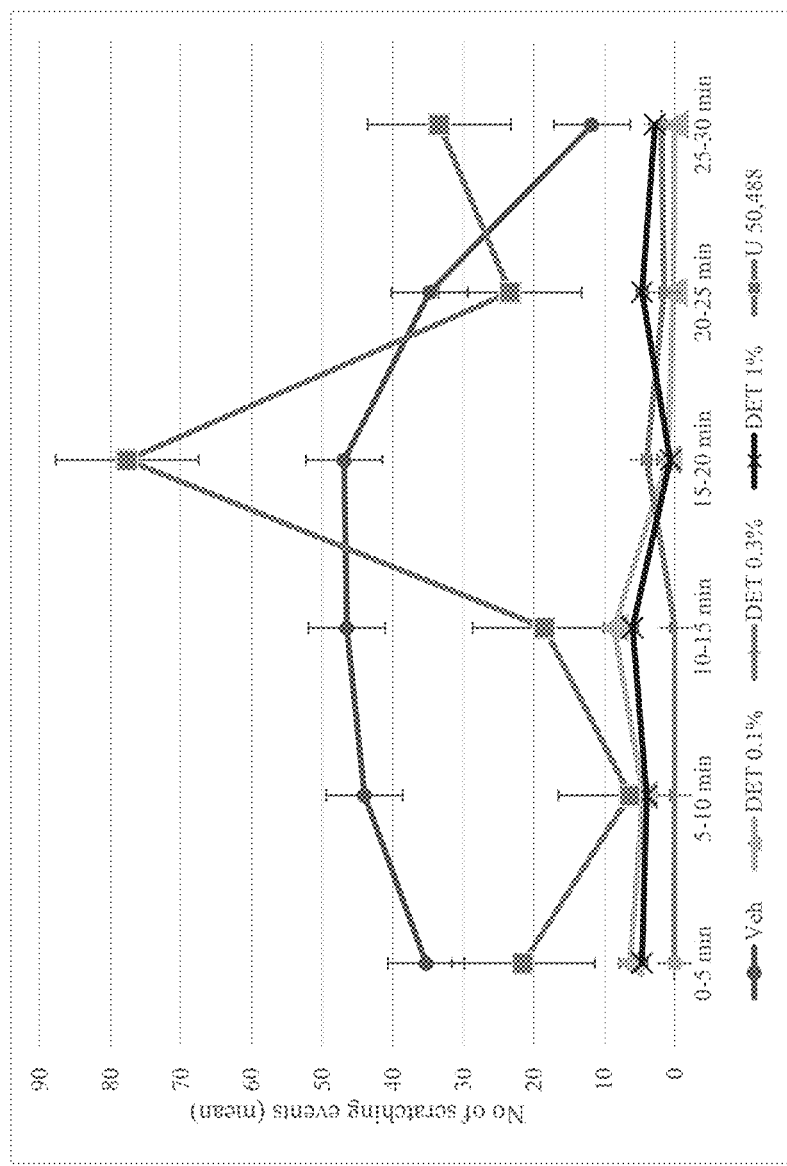
FIG. 3: A graphical representation of scratching events over time.

Each of the topical formulations of Example 1 were each found to reduce the number of scratching events in a statistically significant fashion over each 5 minute time point between time zero and 30 minutes. U-50,488 was found to reduce the number of scratching events in a statistically significant fashion over each 5 minute time point between time zero and 15 minutes. Apart from the death of the 2 mice on Day 4, no other adverse events were noted for any dose tested. A graphical representation of the number of scratching events over time is shown in FIG. 3.

Example 7: Clinical Efficacy of Topical Detomidine

In a double blind, vehicle controlled, randomized crossover design study, the safety and efficacy of topically applied 0.1 and 1 wt % detomidine hydrochloride is assessed for the treatment of pruritus.

The study consists of a Screening Period of up to 7 days during which inclusion/exclusion criteria will be reviewed. Subjects meeting inclusion/exclusion criteria have a score of at least 5 on the 11-Point Numeric Rating Scale (NRS) for Pruritus will complete the one week Screening Period. Subjects will complete a daily diary for NRS for Pruritus scores and Sleep scores. At the end of the Screening Period, subjects who have a NRS for Pruritus score of at least 5 recorded in the diary on at least 4 of the 7 days preceding Day 0 will be eligible to continue. Baseline assessments will be recorded for vital signs, pruritic body surface area, skin integrity, POOL, and laboratory results. The Baseline period will be followed by a 2 week Treatment Period 1 in which subjects will be randomized to 0.1 wt % detomidine hydrochloride gel or Placebo gel to be applied QD for 14 days. During the 2 week Treatment Period subjects will complete daily diaries of NRS for Pruritis scores and Sleep scores. On Day 14 subjects will return to the clinic to review diaries, adverse events (AEs), concomitant medications, and to record body surface area for pruritus, skin integrity, POOL, and laboratory results. Subjects will then enter a Washout Period for up to 56 days until the subject again scores at least 5 on the NRS for Pruritus on 4 consecutive or 4 of the past 7 days or 56 days pass. Subjects will then enter a 2 week Treatment Period 2 during which the same procedures as Treatment Period 1 will be performed except subjects will receive the alternate treatment to that assigned in Treatment Period 1.

We claim:

1. A method of treating notalgia paresthetica in a subject in need thereof comprising topically administering to the subject a pharmaceutical composition comprising 0.01-5 wt % of detomidine.

2. The method of claim 1, wherein the detomidine is detomidine hydrochloride.

3. The method of claim 2, wherein the detomidine hydrochloride is anhydrous detomidine hydrochloride.

4. The method of claim 2, wherein the detomidine hydrochloride is detomidine hydrochloride monohydrate.

5. The method of claim 1, wherein the pharmaceutical composition is in the form of a gel, a cream, an ointment, an emulsion, an emu-gel, a foam, a suspension or a spray-patch.

6. The method of claim 5, wherein the pharmaceutical composition is in the form of a gel.

7. The method of claim 1, wherein the pharmaceutical composition comprises 0.033 wt %, 0.1 wt %, 0.33 wt % or 1 wt % detomidine.

8. The method of claim 7, wherein the pharmaceutical composition comprises 0.1 wt %, detomidine.

9. The method of claim 7, wherein the pharmaceutical composition comprises 0.33 wt %, detomidine.

10. The method of claim 7, wherein the pharmaceutical composition comprises 1 wt %, detomidine.

11. The method of claim 1, wherein the pharmaceutical composition comprises detomidine as the sole active agent.

12. The method of claim 1, further comprising administering to the subject at least one additional active agent.

13. The method of claim 12, wherein the additional active agent is selected from the group consisting of corticosteroids, doxepine, tacrolimus, pimecrolimus, pramoxine, lidocaine, prilocaine, ketamine, amitriptyline, capsaicin, menthol, camphor, strontium, tofacitinib, crisaborole, N-palmitoylethanolamine, an antihistamine, an SNRI, an SSRI, naltrexone, butophanol, nalfurafine, gabapentin, pregabalin, aprepitant, thalidomide, lenalidomide, ursodeoxycholic acid, rifampin, cholestyramine, phenobarbital, Botulinum toxin A, naloxone, ASNO08, SNA-125, TS-022, KPL-716 or orvepitant.

14. The method of claim 12, wherein the additional active agent is administered topically.

15. The method of claim 12, wherein the administration of the additional agent is administered orally or parenterally.

16. The method of claim 1, wherein pharmaceutical composition is administered once daily.

17. The method of claim 1, wherein the pharmaceutical composition is administered twice daily.

18. A method of treating notalgia paresthetica in a subject in need thereof comprising topically administering to the subject a therapeutically effective, substantially non-systemic amount of detomidine.

19. The method of claim 18, wherein the detomidine is administered as a pharmaceutical composition comprising 0.01-5 wt % detomidine.

20. The method of claim 19, wherein the pharmaceutical composition is in the form of a gel, a cream, an ointment, an emulsion, an emu-gel, a foam, a suspension or a spray-patch.

* * * * *